United States Patent [19]

Miyamoto

[11] Patent Number: 5,602,029
[45] Date of Patent: Feb. 11, 1997

[54] METHOD FOR FABRICATING SUBSTRATE FOR CELL CULTURE AND METHOD FOR CELL ARRANGEMENTS

[75] Inventor: Shigeyuki Miyamoto, Tokyo, Japan

[73] Assignee: NEC Corporation, Tokyo, Japan

[21] Appl. No.: 493,415

[22] Filed: Jun. 22, 1995

[30] Foreign Application Priority Data

Jun. 27, 1994 [JP] Japan ................................ 6-144277

[51] Int. Cl.⁶ ........................ C12N 5/00; C12N 11/00; C12M 1/40
[52] U.S. Cl. ................... 435/395; 435/305.1; 435/174; 435/396; 435/401; 435/402
[58] Field of Search ......................... 435/174, 177–180, 435/182, 240.1, 240.2, 240.23, 240.241, 240.243, 817, 287.9, 288.3, 297.1, 297.5, 305.1

[56] References Cited

U.S. PATENT DOCUMENTS

| | | | |
|---|---|---|---|
| 4,103,073 | 7/1978 | McAlear et al. | 428/474 |
| 4,634,628 | 1/1987 | Munakata et al. | 430/325 |
| 5,108,926 | 4/1992 | Klebe | 435/240.243 |
| 5,202,227 | 4/1993 | Matsuda et al. | 435/240.23 |
| 5,470,739 | 11/1995 | Akaike et al. | 436/240.243 |

FOREIGN PATENT DOCUMENTS

| | | |
|---|---|---|
| 62-228274 | 10/1987 | Japan. |
| 63-111454 | 5/1988 | Japan. |
| 63-186139 | 8/1988 | Japan. |
| 1-291791 | 11/1989 | Japan. |
| 2-245181 | 9/1990 | Japan. |
| 3-7576 | 1/1991 | Japan. |
| 3-7577 | 1/1991 | Japan. |
| 4-322657 | 11/1992 | Japan ............. 435/240.243 |
| 5-176753 | 7/1993 | Japan. |

*Primary Examiner*—William H. Beisner
*Attorney, Agent, or Firm*—Sughrue, Mion, Zinn, Macpeak & Seas

[57] ABSTRACT

The substrate for cell culture to be used for cell arrangements is formed by applying a photoresist on a surface of a substrate, removing selective parts of the photoresist on the surface of the substrate by optical exposure and development, and forming an immobilized enzyme membrane on the surface of the substrate after removing the photoresist, and removing the photoresist after forming the immobilized enzyme membrane. An enzyme substrate of enzyme contained in the immobilized enzyme membrane is a material that is necessary for growth of cells for forming cell arrangements or is a material that inhibits growth of such cells, and a reaction product of oxygen contained in the immobilized enzyme membrane is a material that is necessary for growth of cells for forming cell arrangements or a material that inhibits growth of such cells. It is possible to control the cell adhesion on the surface of the substrate.

6 Claims, 3 Drawing Sheets

METHOD FOR FABRICATING SUBSTRATE FOR CELL CULTURE AND METHOD FOR CELL ARRANGEMENTS

BACKGROUND OF THE INVENTION

1. Field of the Invention

The present invention relates to a substrate for a cell culture, a method for fabricating such a substrate, and a method for forming cell arrangements using such a substrate.

2. Description of the Related Art

At present the culture of cells of various animals or plants is being carried out, and methods for culturing new cells are being developed. Cell culture technology is being used for the elucidation of the chemical phenomena and properties of cells, and for the examination of the physiology and poisonous properties of artificially synthesized chemicals.

Some types of cells, particularly many animal cells, adhere to something, have an adhesion dependency for growing, and cannot live for a long time in a floating condition outside of a living body. For the culturing of these types of cells having an adhesion dependency, a carrier is necessary for cell adhesion. In general, a plastic type of culture dish is used in which a cell bonding protein, such as collagen or fibronectine, is uniformly applied. It is known that the cell bonding protein acts on the culturing cells, makes the cell adhesion easy, and has an effect on the shape of the cells.

On the other hand, technology has been reported for producing certain arrangements of culture cells by making the culture cells adhere to an ultra-small area of a substrate. By using this type of technology, culture cells have possible applications such as artificial internal organs, biosensors, and bioreactors. As a method for the arrangement of culture cells, use is made of a substrate that has a patterned surface upon which the ease of adhesion differs with respect to a cell. An arrangement of cells is achieved by culturing cells on this surface and by allowing the cells to adhere only on the surface processed for the cells to adhere to.

For example, in Japanese Patent Application Kokai Publication No. Hei. 2-245181, for the purpose of breeding nerve cells in the form of a circuit, a culture cell is used as a charge storage medium that has been formed by electrostatic patterning. Further, in Japanese Patent Application Kokai Publication No. Hei. 3-7576, trials have been made of arranging culture cells on a patterned surface by a photolithographic method using a cell adhesive or a cell nonadhesive photosensitive hydrophilic polymer. Further, as reported in Japanese Patent Application Kokai Publication No. Hei. 3-7577, cell adhesive groups have been introduced into cell culture material having a cell nonadhesive surface and cell adhesive functional groups induced by irradiating it with ultraviolet light or radiation. Then, adhesive or nonadhesive monomers are applied on top of this, the surface is patterned, and, in this way, the arrangement of the cells is controlled.

Furthermore, Japanese Patent Application Kokai Publication No. Hei. 5-176753 reports on a substrate for cell culture that is patterned with collagen that has an effect on the cell attaching efficiency and form, and on a method for fabricating the substrate using photolithography. By culturing cells on such a substrate, many cells attach to collagen that has been patterned into the surface, and patterning of the cells is realized.

In conventional substrates for cell culture used for the formation of cell arrangements, the cell adhesivity of the substrate surface is fixed. That is, it has not been possible to change the cell adhesion surface of a prepared substrate to a nonadhesive surface, or conversely, to change the cell nonadhesive surface to a cell adhesive surface. Also, it has been extremely difficult to obtain more than two arrangements of cells with the conventional substrates for cell culture.

SUMMARY OF THE INVENTION

An object of the invention is to overcome the problems existing in the prior art and to provide a method for fabricating a substrate for cell culture to be used for cell arrangements, in which it is possible to control the cell adhesion on a surface of the substrate, and a method for forming cell arrangements using such a substrate.

According to one aspect of the invention, there is provided a substrate for cell culture for forming cell arrangements thereon, the substrate comprising:

a substrate on which adhesive cells adhere and grow for cell arrangements; and an immobilized enzyme membrane which is formed on selective parts of a surface of the substrate.

According to second aspect of the invention, there is provided a method for fabricating a substrate for cell culture comprising the steps of:

applying a photoresist on a surface of a substrate;

removing selective parts of the photoresist on the surface of the substrate by optical exposure and development;

forming an immobilized enzyme membrane on the surface of the substrate after removing the photoresist; and removing the photoresist after forming the immobilized enzyme membrane.

The substrate for cell culture of this invention has an immobilized enzyme membrane formed on parts of the substrate surface. When the substrate is soaked in a culture medium containing enzyme substrates for the immobilized enzyme membrane, the enzyme substrates in the culture medium are consumed by the enzyme of the immobilized enzyme membrane, and the corresponding products generated are then formed on the enzyme membrane surface. As a result of that, compared with the surface where no immobilized enzyme membrane is provided, the concentration of the localized enzyme substrates of the immobilized enzyme membrane surface is low, and the concentration of the generated products becomes high. That is, using the substrate for cell culture of this invention, if cell culturing is carried out in a culture medium containing enzyme substrates, these enzyme substrates are necessary for growth of cells, or if the products that are generated are such that they inhibit the growth of cells, then the attaching and growth of cells onto the immobilized enzymes membrane surface is suppressed. However, if the enzyme substrates are products that inhibit the growth of cells, or if the generated products are products that are necessary for the growth of cells, then the growth and attaching of cells onto the immobilized enzyme membrane surface will be promoted. By this type of mechanism the desired cell pattern can be realized onto the substrate surface.

Further, the concentration of the localized enzyme substrates or locally generated products of the immobilized enzyme membrane surface changes according to the concentration of the enzyme substrates contained in the culture medium, and by controlling the concentration of enzyme substrates contained in the culture medium, the cell adhesivity onto the immobilized enzyme membrane surface and cell growth can be controlled. For example, in the case where cells are cultured by a substrate for cell culture in which the reaction products of oxygen contained in the immobilized enzyme membrane inhibit cell growth, if use is made of the culture medium that includes enzyme substrates, the generated products are formed on the immobilized enzyme membrane surface so that adhesion of the cells onto the immobilized enzyme membrane surface is suppressed. However, if the culture medium that does not contain enzyme substrates is used, the concentration of the localized generated products of the immobilized enzyme membrane surface is zero so that the cell adhesion suppression effect due to the immobilized enzyme membrane disappears and the cells adhere to the immobilized enzyme membrane surface and develop. In this way, depending on the concentration of the enzyme substrates contained in the culture medium, it is possible to change the immobilized enzyme membrane surface into a cell nonadhesive surface or a cell adhesive surface.

Furthermore, by using the substrate for cell culture of this invention, it is easily possible to attain more than two types of cell arrangements. For example, in the case when cells are cultured by a substrate for cell culture where the reaction products of oxygen contained in the immobilized enzyme membrane inhibit cell growth, firstly, if a first type of cell is cultured by a culture medium that includes the enzyme substrates, the cells adhere avoiding the immobilized enzyme membrane surface. Next, if a second type of cell is cultured by a medium that does not include the enzyme substrates, the cells adhere to the immobilized enzyme membrane surface and grow. In this way, the first type of cell adheres to all surfaces apart from the immobilized enzyme surface membrane of the substrate for cell culture, and the second type of cell adheres to the immobilized enzyme surface membrane of the substrate for cell culture, and it is possible to obtain two types of cells arrangements.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENTS OF THE INVENTION

Now, preferred embodiments of the invention are described with reference to the attached drawings.

Figure 1A:
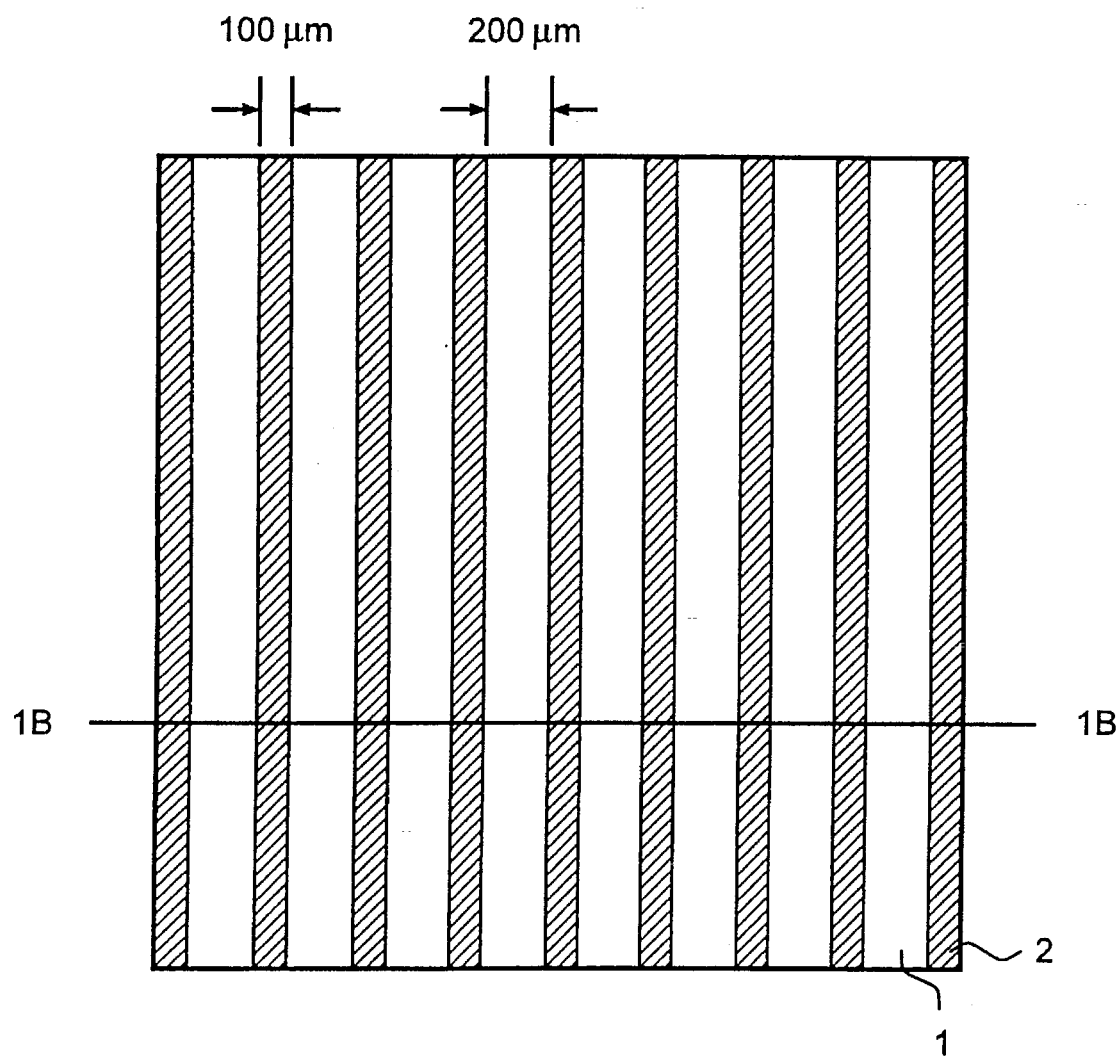
FIG. 1A is a plan view of a cell culture substrate of a first embodiment according to the invention.
Figure 1B:
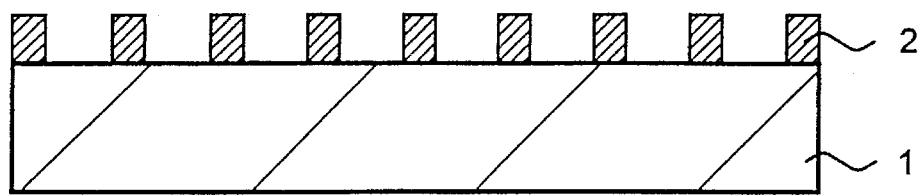
FIG. 1B is a cross sectional view of the same taken along line 1B—1B in FIG. 1A.

FIG. 1A is a plan view of the cell culture substrate of a first embodiment of the invention, and FIG. 1B is a cross sectional view of the same taken along line 1B—1B. The substrate for cell culture is itself a 0.5 mm thick quartz substrate. As an immobilized enzyme membrane, a striped pattern consisting of a 100 μm wide immobilized glucose oxidase membrane 2 with a separation of 200 μm is formed on the substrate surface. The immobilized glucose oxidase membrane consists of an immobilized glucose oxidase that has the glutal-aldehyde crosslinking membrane of bovine serum albumin as its base.

The materials used for the cell culture substrate are glass, quartz, silicon, metal, and polystyrene. Transparent glass, quartz, and polystyrene are especially suited for transparent microscopic observation of culture cells.

It is sufficient if the enzyme contained in the immobilized enzyme membrane provided in the cell culture substrate is such that its nature or its growth substance is necessary for cell growth, or if it is a substance that inhibits cell growth. In the case of glucose oxidase, the glucose and oxygen necessary for cell growth are consumed and the hydrogen peroxide that inhibits growth is formed, and it is suitable for application to this invention. Also, apart from this, urease, uricase, lactate oxidase, alcohol-oxidase, lactate dehydrogenase, alcohol dehydrogenase can be used.

A general enzyme fixing material can be used for the base of the immobilized enzyme membrane provided in the cell culture substrate. Apart from the bovine serum albumin used, collagen, alginic acid gel, polyvinyl alcohol, or polyacrylamide can be used.

Collagen adsorption pre-treatment of the whole substrate surface can be carried out in order to improve the cell adhesivity of the cell culture substrate. Further, the immobilized enzyme membrane provided in the cell culture substrate of this embodiment is of a single type. If, however, more than two types of immobilized enzyme membranes are provided, the cell adhesivity of the surface of each immobilized enzyme membrane can be controlled independently, and it is possible to obtain even more complicated cell arrangements.

Figure 2A:
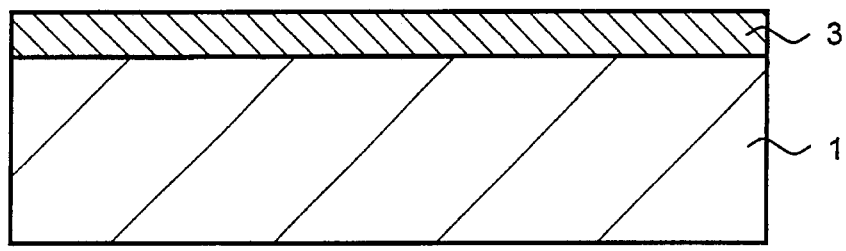
FIGS. 2A–2D are cross sectional views of the substrate being processed for explaining the fabrication method of the first embodiment of the cell culture substrate according to the invention.
Figure 2B:
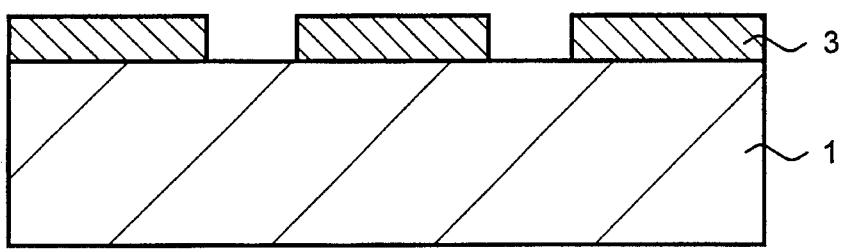
Figure 2C:
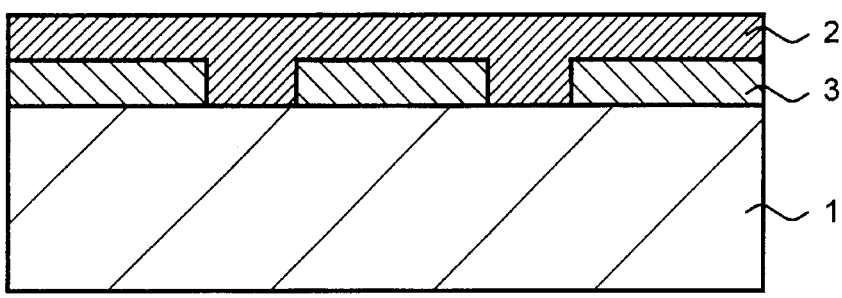
Figure 2D:
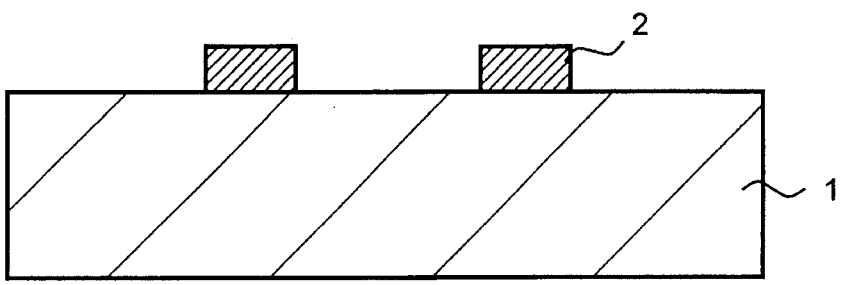

FIGS. 2A–2D show cross sectional views of the structure being processed for explaining the processing steps of the fabrication method of the cell culture substrate of a second embodiment of the invention. First, as shown in FIG. 2A, photoresist 3 (Shipley Microposit MP 1300-37) is applied to a quartz substrate by spinning at 3000 rpm for 30 seconds and the substrate is then dried at 90° C. for 30 minutes. At this time, a reagent such as hexamethyldisilazane can be used in pre-conditioning the substrate to improve the adhesivity of the photoresist and the substrate. Next, mercury lamp is irradiated onto the substrate through the photoresist, development is carried out (Shipley Microposit MF-312), and, as shown in FIG. 2B, the photoresist of the region is removed where the immobilized enzyme membrane is formed. After this, 60 mg/ml glucose oxidase, 1% glutal-aldehyde incorporating 15% bovine serum albumin 0.6 milliliter, is applied to the substrate by spinning at 3000 rpm for 30 seconds. At this time, a reagent such as amino-propyltriethoxysilane can be used in pre-conditioning the substrate to improve the adhesivity of the photoresist and the substrate. After that, as shown in FIG. 2C, the immobilized glucose oxidase membrane 2 is formed by being left alone at 20° C. for 1 minute and proceeding with the crosslinking membrane. Finally, the substrate is soaked in acetone, the photoresist is dissolved, washed in water and, as shown in FIG. 2D, the cell culture substrate is obtained.

Now the cell arrangement fabrication method as a third embodiment of the invention will be described. The size of the cell culture substrate is 20 mm×15 mm, and was fabricated in the same way as the second embodiment. The immobilized glucose oxidase is formed on one of the substrate surface of 10 mm×15 mm, and the remaining half of 10 mm×15 mm of the quartz is exposed. In order to improve the adhesivity of the substrate it was soaked in 0.03% collagen water solution for one hour.

After this, the substrate is sterilized by being soaked in ethanol and being dried, and it is put in a transparent square polyethylene culture container having a bottom surface area of 20 mm×15 mm, height 10 mm, and a thickness of 0.5 mm. Human umbilical vein endothelial cell of Morinaga Biochemical Laboratory was plated into the culture container. MCDB104 liquid culture medium, a product of Nissui Pharmaceutical Company Ltd., was used as the culture medium into which 10 ng/ml fibroblast growth factor was added. The culture container into which the cell was sown was cultivated for 12 hours in an incubator in a saturated atmosphere of 5% carbon dioxide at 37° C., and the substrate onto which the cell adhered to was observed by a microscope.

Figure 3A:
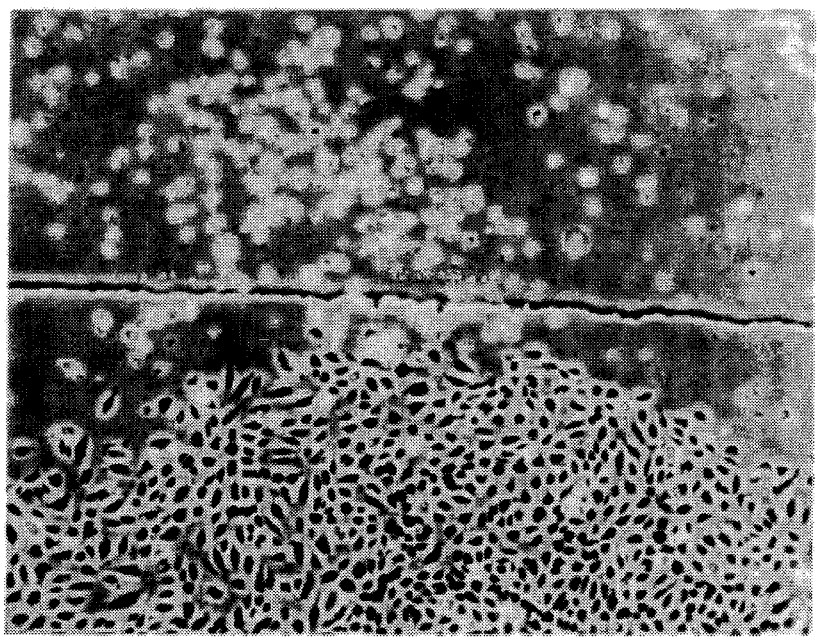
FIG. 3A is an image of the microscope photograph of the substrate obtained by the first embodiment of the fabrication method of the cell arrangement method of this invention.

FIG. 3A is an image diagram of a microscope photograph of a substrate surface obtained by this embodiment. Immobilized glucose oxidase membrane is formed in the upper half of the photograph, and immobilized glucose oxidase membrane is not formed on the lower half, where the quartz substrate is exposed. The cells do not adhere to the areas where immobilized glucose oxidase membrane is formed and only adhere to the surface of the quartz substrate that is exposed.

Figure 3B:
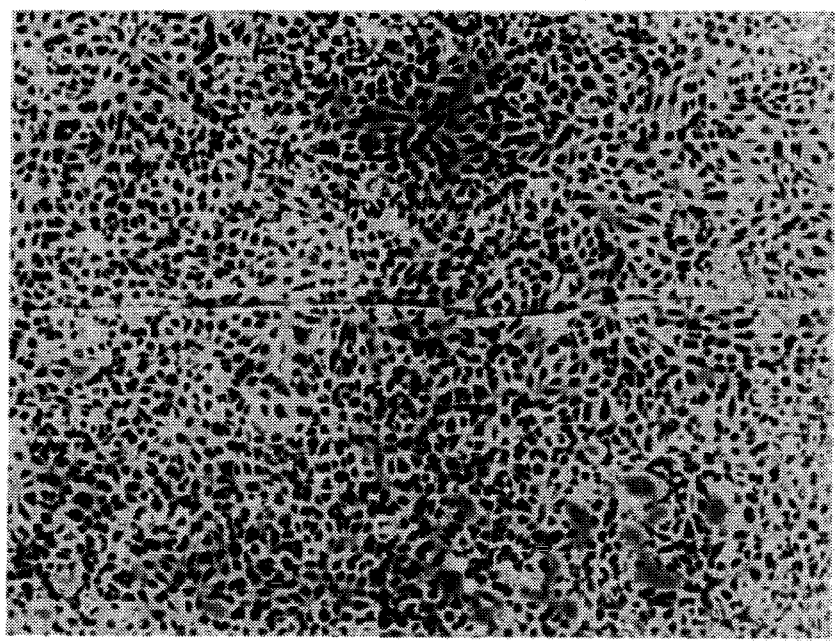
FIG. 3B is an image microscope photograph of the substrate surface as an example for comparison in the case where an albumin membrane is used.

FIG. 3B is an image microscope photograph of the substrate surface as an example for comparison in the case where an albumin membrane, that does not include glucose oxidase, is used for forming the cell culture substrate instead of an immobilized glucose oxidase membrane. The albumin membrane is formed on the upper half and the lower half is the exposed quartz substrate surface. The difference with FIG. 3A is that cells have adhered to the entire area. From this it can be understood that the immobilized glucose oxidase membrane inhibits cell adhesivity and growth.

The inhibition of cell adhesivity and growth due to the immobilized glucose oxidase membrane is thought to occur due to the following mechanism. The MCDB104 culture medium contains 720 mg/l of glucose and, if the cell culture substrate on which an immobilized glucose oxidase membrane has been formed is soaked, then an oxidation reaction of the glucose inside the membrane progresses. This reaction consumes the glucose and oxygen that are necessary for cell growth, and is a reaction that leads to the formation of hydrogen peroxide that inhibits the cell growth. The cell adhesion and growth of the membrane surface is inhibited for these reasons.

Further, if the formation of the cell arrangement according to this method is carried out using a culture medium that does not include glucose, because the culture medium does not include glucose, the number of adhered cells is small compared with FIG. 3A, and the cells adhere to the entire area.

The cells that are suitable for this method of forming cell arrangements are enzyme substrates contained in the immobilized enzyme membrane, or those that are necessary for the growth of the cells for attaining the arrangements, or conversely, those that are sufficient to satisfy the conditions for inhibiting growth, so that the cells are not limited to those of endothelial cell. The immobilized glucose oxidase membrane formed on the cell culture substrate used for this embodiment, consumes glucose and oxygen and is suitable for the large majority of cells. However, if the cell is very sensitive to a certain special product or if it is a cell that has requirements, then this product is consumed, or by using a cell culture substrate that uses a forming enzyme, the method for forming cell arrangement becomes especially different with respect to this cell.

According to the invention, by using the cell culture substrate of this invention, it is possible to control the cell adhesion onto the immobilized enzyme membrane that is formed on the substrate surface by the enzyme substrate concentration contained in the culture medium used. That is, it is possible to carry out the ON/OFF of cell adhesion onto the immobilized enzyme membrane surface by using the enzyme substrates in the culture medium as a switch. Further, by using the cell culture substrate of this invention, it is possible to obtain arrangements of more than two types of cells and it is easy to apply the culture cell to artificial organs and biosensors.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A method for selectively arranging cells on a substrate, said method comprising the steps of:

providing a substrate with at least a first and a second substrate area, said first substrate area having deposited thereon an immobile enzyme membrane, said second substrate area not having said immobile enzyme membrane;

selecting at least one of said first and said second substrate area as a selected cell cultivation area of said substrate for cell cultivation;

determining for a culture medium a constant enzyme substrate concentration of 0 or greater on the basis of the selection for cell cultivation; and exposing said substrate to the culture medium, containing said concentration of enzyme substrates, to arrange said cells on said selected cell cultivation area.

2. The method as set forth in claim 1, wherein said providing step is performed according to the steps of:

applying a photoresist layer on a surface of a substrate;

removing portions of said photoresist layer corresponding to said first substrate area;

forming an immobilized enzyme membrane layer on said surface; and removing a remainder of said photoresist layer corresponding to said second substrate area and portions of said immobilized enzyme membrane layer formed on said remainder.

3. A system for culturing cells in a preselected arrangement, comprising:

first cells to be cultured in said arrangement;

a first cell culture medium for maintaining said first cells;

a cell culture substrate comprising (1) a supportive substrate, and (2) a first immobilized enzyme membrane pattern which includes a first enzyme, and which is selectively disposed over said supportive substrate; and a first enzyme substrate of said first enzyme, said first enzyme substrate being acted upon by said first enzyme substrate upon combination therewith;

wherein said first cells and said first cell culture medium are combined with said cell culture substrate to define a first cell culture environment; and wherein said first enzyme substrate is included in said first cell culture environment in a first preselected concentration to control an adhesivity of said first cells to said first immobilized enzyme membrane pattern, said first preselected concentration being in the range of zero or greater.

4. The system as set forth in claim 3, further comprising:

second cells to be cultured in said arrangement;

a second cell culture medium for maintaining said second cells;

a second immobilized enzyme membrane pattern which includes a second enzyme different from said first enzyme, and which is selectively disposed over said supportive substrate; and a second enzyme substrate of said second enzyme, said second enzyme substrate being acted upon by said second enzyme upon combination therewith;

wherein said second cells and said second cell culture media are combined with said cell culture substrate to define a second cell culture environment; and wherein said second enzyme substrate is included in said second cell culture environment in a second preselected concentration to control an adhesivity of said second cells to said second immobilized enzyme membrane pattern, said second preselected concentration being in the range of zero or greater.

5. A cell culture substrate on which cultured cell arrangements are selectively formed, comprising:

a substrate on which adhesive cells adhere and grow to produce cell arrangements; and an immobilized enzyme membrane provided on selected parts of a surface of said substrate, said immobilized enzyme membrane comprising an enzyme;

wherein said enzyme is one which reacts to the presence, in a cell culture medium, of enzyme substrates of said enzyme, to encourage or to inhibit growth of said cell arrangements on said immobilized enzyme membrane.

6. A cell culture substrate on which cultured cell arrangements are selectively formed, comprising:

a substrate on which adhesive cells adhere and grow to produce cell arrangements; and an immobilized enzyme membrane provided on selected parts of a surface of said substrate, said immobilized enzyme membrane comprising an enzyme;

wherein said enzyme is one which reacts to the presence, in a cell culture medium, of enzyme substrates of said enzyme, to produce a reaction product which encourages or inhibits growth of said cell arrangements on said immobilized enzyme membrane.

* * * * *